(12) United States Patent
Ford et al.

(10) Patent No.: US 9,242,934 B2
(45) Date of Patent: Jan. 26, 2016

(54) PROCESS FOR THE PREPARATION OF OXINDOLES AND ORTHO-SUBSTITUTED ANILINES AND THEIR USE AS INTERMEDIATES FOR SYNTHESES

(71) Applicant: Bayer CropScience AG, Monheim (DE)

(72) Inventors: Mark James Ford, Schmitten (DE); Gunter Karig, Hofheim am Taunus (DE)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 13/915,898

(22) Filed: Jun. 12, 2013

(65) Prior Publication Data
US 2013/0281711 A1 Oct. 24, 2013

Related U.S. Application Data

(62) Division of application No. 12/769,302, filed on Apr. 28, 2010, now Pat. No. 8,492,590.

(30) Foreign Application Priority Data

May 2, 2009 (EP) .................................. 09006050

(51) Int. Cl.
C07D 209/34 (2006.01)
C07C 323/58 (2006.01)
(52) U.S. Cl.
CPC ............ C07D 209/34 (2013.01); C07C 323/58 (2013.01)
(58) Field of Classification Search
CPC .................................................. C07D 209/34
USPC ............................................... 548/485, 486
See application file for complete search history.

(56) References Cited

U.S. PATENT DOCUMENTS 3,972,894 A 8/1976 Gassman
4,690,943 A 9/1987 Kadin
(Continued)

FOREIGN PATENT DOCUMENTS

EP 0636608 A1 2/1995
JP 2008101014 A 5/2008
WO 9641799 A1 12/1996

OTHER PUBLICATIONS

Jiang et al.., "Design, Systhesis, and Biological Evaluations of Novel Oxindoles as HIV-1 Non-Nucleoside Reverse Transcriptase Inhibitors," Bioorganic & Medicinal Chemistry Letters, pp. 2109-2112, (2006).

(Continued)

Primary Examiner — Shawquia Jackson
(74) Attorney, Agent, or Firm — Miles & Stockbridge PC

(57) ABSTRACT

The present invention relates to processes for the preparation of oxindoles and ortho-substituted anilines and their use as intermediates for syntheses. The invention further relates to a process for the preparation of compounds of formula (4):

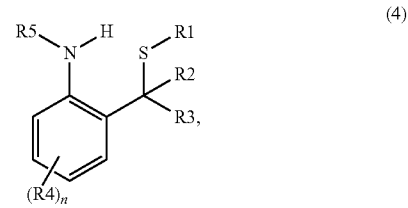

where a mixture of an aniline (compound of formula Q) is reacted with a thioether (compound of formula W):

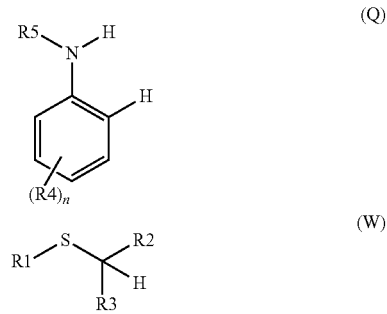

in the presence of a chlorinating agent and an organic solvent at a reaction temperature in the range above −65° C.

In a subsequent process, this compound is further reacted in the presence of an acid catalyst to give the indole of formula (7) or the oxindole of formula (8):

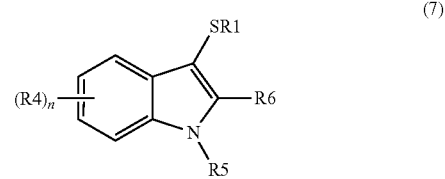

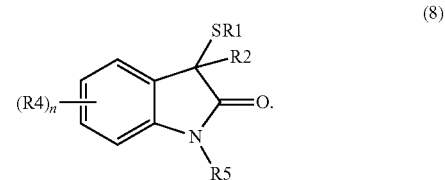

12 Claims, No Drawings

(56) References Cited

U.S. PATENT DOCUMENTS 5,663,431 A 9/1997 Di Malta et al.
2005/0090541 A1 4/2005 Arnaiz et al.

OTHER PUBLICATIONS

Sumpter, "The Chemistry of Oxindole," Chem. Rv., pp. 443-479, (1945).
Zard et al., "A New and Practical Systhesis of Indolones," Tetrahedron Letters, pp. 9553-9557, (1994).
Zard et al., "A New Radical Based Systhesis of Lactams and Indolones from Dithiocarbonates (Xanthates)," Tetra. Ltrs. pp. 1719-1722, (1994).
Jones et al., "Intramolecular Reations Using Amide Links: Aryl Radical Cyclisation of Silylated Acryloylandilides," Tetra. Ltrs. pp. 7673-7676, (1994).
Kikugawa et al., "Intramolecular Cyclization with Nitrenium Ions Generated From N-Chlloro-N-Methodxyamides in Neutral Condition," Chem. Ltrs. pp. 1771-1774, (1987).
Clark et all., "Preparation of Indoles and Oxindoles from N-(Tert-Butoxycarbonyl)-2-Alkylanilines," Systhesis, pp. 871-878, (1991).
Yonemitsu et al., "Photochemical Systhesis of 1,2,3,4-Tetrahydroisoquinolin-3-Ones and Oxindoles from N-Chloracetyl Derivatives of Benzylamines and Anilines. Role of Intramolecular Exciplex Formation ANS/CIS CQNFORMATION of Amide Bonds," Chem. Pharm. Bull. pp. 128-136, (1981).
Gassman et al., Indoles From Anilines: Ethyl 2-Methylindole-5-Carboxylate, Org. Synthesis Coll., vol. 56, pp. 72-76.
Gassman et al., Indoles From Anilines: Ethyl 2-Methylindole-5-Carboxylate, Org. Synthesis Coll., vol. 6, pp. 601-605.
Gassman et al., "Oxindoles . A New, General Method of Synthesis," J. Am. Chem., Soc., pp. 5508-5512, (1974).
Gassmann et al., "Generation of Azasulfonium Salts from Halogen-Sulfide Complexes and Anilines. The Synthesis of Indoles, Oxindoles, and Aldylated Aromatic Amines Bearing Cation Stablizing Substituents," J. Am. Chem Soc., pp. 5512-5517 (1974).
Johnson et al., "General Procedure for the Synthesis of 0-Aminophenylacetates by a Modification of Gassman Reaction," J. Org. Chem, pp. 1374-1375, (1990).
Warpehoski, "Total Synthesis of U-71,184, A Potent New Antitumor Agent Modeled on CC-1065," Tetra. Ltrs., pp. 4103-4106, (1986).
Wright et al., "A Convenient Modification of the Gassman Oxindole Synthesis," Tetra. Ltrs., pp. 4631-4634, (1995).
Lengyel et al., "t-Butyl Hypochlorite: A Powerful Electrophilic Aromatic Ring Chlorinating Agent," Synthesis Comm. pp. 1891-1896, (1998).
Wierenga et al., "A Versatile and Efficient Process to 3-Substituted Indoles from Anilines," Tetra. Ltrs., pp. 2437-2440, (1983).
Delimoge et al., "Simple Syntheti Routes to 5-(3,6-Dhyro-2-OXO-2H-1,3,4-Thiadiazin-5-YL)-1H-Indole 2,3-Diones and their Derivatives," SmithKline Beecham, Labratories, pp. 1525-1532, (Oct. 1991).
Walsh et al., "Antiinflammatory Agents. 3, Synthesis and Pharmacological Evaluation of 2-Amino-3-Benzoylphenylacetic Acid and Analogues," J. Med. Chem., pp. 1379-1388, (1984).
Connolly et al., "Metal Hydride Mediated Reduction of 1,3-Dimethylthio)Oxindole," J. Chem. pp. 542-546, (1997).
Connolly et al., "Non-Reductive Desulfenylation of 3-Thioalkyl-2-Oxindoles," Syn. Lett., pp. 663-664, (1996).
International Search Report Based on PCT/EP2010/002566, Dated Jun. 5, 2010.
Gassman et al., ":Thermal Rearrangement of N-Chloroanilines Evidence of the Intermediacy of Nitreniums Ions1," J. Am. Chem. Soc., vol. 96, No. 17, pp. 5508-5512, (1974).

PROCESS FOR THE PREPARATION OF OXINDOLES AND ORTHO-SUBSTITUTED ANILINES AND THEIR USE AS INTERMEDIATES FOR SYNTHESES

CROSS REFERENCE TO RELATED APPLICATIONS

This application is a Divisional application of U.S. application Ser. No. 12/769,302, filed Apr. 28, 2010, which claims priority to European Application No. 09006050.0, filed May 2, 2009, the content of all of which are incorporated herein by reference in their entireties.

BACKGROUND OF THE INVENTION

1. Field of the Invention

The invention relates to the technical field of the chemical synthesis of biologically active compounds, preferably for intermediates for the synthesis of fine chemicals and active ingredients from pharmacy and/or agriculture.

2. Description of Related Art

In principle, the selective exchange of hydrogen on an aromatic system with a substituted carbon atom belongs to one of the fundamental reactions in organic chemistry and is therefore known.

One class of compounds which can be prepared in this way is, for example, optionally substituted 3-alkylthioindol-2-ones (3-(alkylsulfanyl)-1,3-dihydro-2H-indol-2-ones), which can in turn be converted to optionally substituted 2-oxindoles (1,3-dihydro-2H-indol-2-ones). Optionally substituted oxindoles and their precursors, such as optionally substituted 3-alkylthioindol-2-ones, are versatile intermediates for active ingredient syntheses (Bioorg. Med. Chem. Lett. 2006, 16, 2109; JP 2008-101014; WO 96/41799 A1). Further uses as precursors to pharmaceutical compounds are described in: US 2005/0090541 A1, EP 636608 A, U.S. Pat. No. 4,690,943A. Most of the described various syntheses of oxindoles use a variation of a Friedel-Crafts reaction (Stolle Synthesis, W. C. Sumpter, Chem. Rev. 1945, 37, 443-449). However, Stolle syntheses can only be used with restrictions since they require strongly acidic conditions and an electron-rich aniline. In addition, however, radical, nitrenium ion and organolithium reactions, and also photochemically dependent methods are also known. However, these are also limited by the type of oxindoles to be prepared, the compatibility of substrates, the reaction conditions, and also by the fact that the aromatic must already have a halogen substituent which is then replaced. (Radical processes: Zard et al., Tetrahedron Lett. 1994, 35, 9553-9556; Zard et al., Tetrahedron Lett. 1994, 35, 1719-1722; Jones et al., Tetrahedron Lett. 1994, 35, 7673-7676; Kikugawa et al., Chem. Letters 1987, 1771-1774; Clark et al., Synthesis 1991, 871-878; Yonemitsu et. al., Chem. Pharm. Bull. 1981, 29, 128-136; see scheme 1).

Scheme 1-Known oxindole syntheses:

(a)

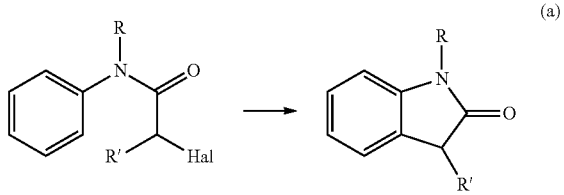

-continued (b)

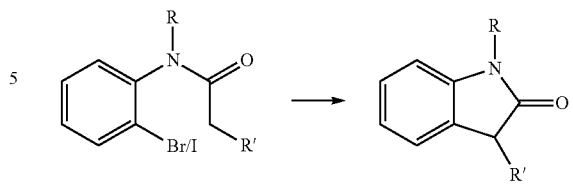

The process by Gassman et al. (Organic Synthesis Coll., vol. 6, 601 and vol. 56, 72), which proceeds from aniline and methyl thioacetate ester via chlorination and treatment with triethylamine at −70° C., appears suitable with regard to feasibility, availability of starting materials, short reaction rate and reproducibility. However, it is also described that good yields can only be achieved if the unstable N-chloro (1) or N-sulfonium (2) intermediates are formed below −65° C., in the normal case at −78° C. (Gassman et. al., J. Am. Chem. Soc., 1974, 96(17), 5508; Gassman et al., J. Am. Chem. Soc., 1974, 96(17), 5512; WO 96/41799 A1; see scheme 2).

Scheme 2-Reaction via aniline chlorination:

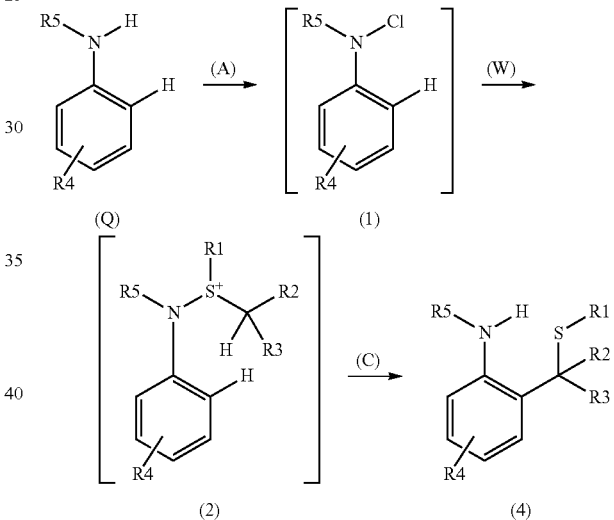

Q = aniline
A = chlorinating agent (e.g.: tert-butyl hypochlorite, t-BuOCl)
W = thioether (R1—S—CHR2R3)
C = tertiary amine base (e.g.: triethylamine)

The chlorinating agent of choice according to the literature is the unstable and explosive tert-butyl hypochlorite since the by-product of the chlorination then gives the neutral tert-butyl alcohol. In the few cases in which sulfuryl chloride ($SO_2Cl_2$) has been used, a second, non-nucleophilic base, such as "proton sponge", has been used (Johnson, J. Org. Chem. 1990, 55, 1374; Warpehoski, Tetrahedron Lett. 1986, 27, 4103). Since both variants are carried out at low temperatures, however, this is not a practicable solution on an industrial scale.

Wright et al. (Tetrahedron Lett. 1996, 37, 4631) describe an alternative where the chlorosulfonium intermediate (3) has been prepared from a sulfoxide and oxalyl chloride (see scheme 3). Here, the chlorosulfonium intermediate (3) is likewise unstable. For this reaction, the sulfoxide must first be prepared and isolated. For reasons of stability, the reaction must proceed at −78° C. and, in order to avoid a reaction between aniline and oxalyl chloride, the reaction is carried out in stages.

Scheme 3-Reaction via chlorosulfonium intermediate:

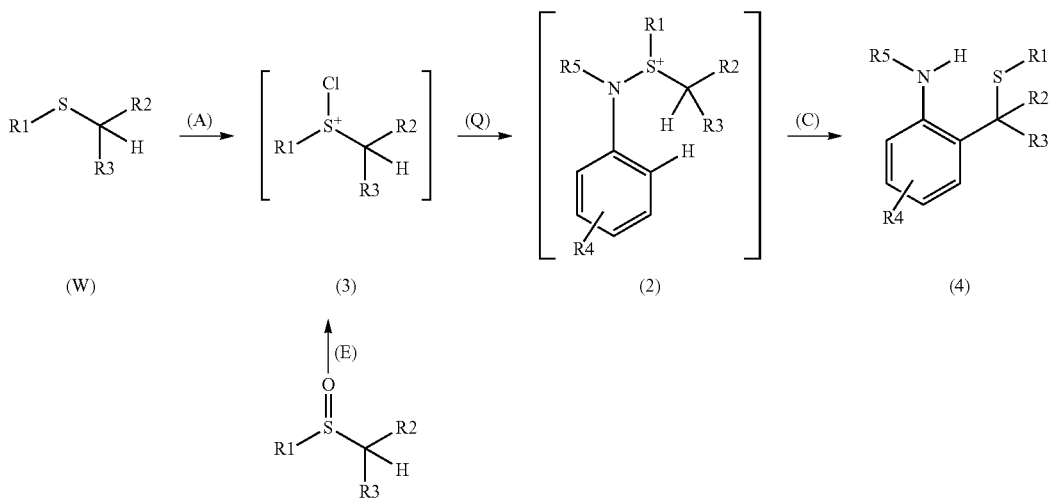

W = thioether (R1—S—CHR2R3)
A = chlorinating agent (e.g.: tert-butyl hypochlorite, t-BuOCl)
Q = aniline
C = tertiary amine base (e.g.: triethylamine)
E = oxalyl chloride (COCl$_2$)

The compounds (4) described by this process (scheme 2 or scheme 3) can only be prepared because of the mechanism of the reaction via the compounds (2). Inevitably here, the use of a base (C) is required for the rearrangement to the compounds (4). In the literature, an additional base to the aniline (compounds of formula Q) such as "proton sponge" or triethylamine is specified for this purpose. The additional base used in these processes must inevitably be recovered in the case of syntheses on an industrial scale and be separated from the unreacted compounds of formula Q in order to be able to use the reisolated compounds of formula Q again as starting materials.

The reasons why the reaction is so sensitive to reaction temperatures above –70° C. and why it has always been carried out in stages are manifold.

Firstly, the functional groups which participate in the reaction, i.e. the nitrogen atom of the aniline and the sulfur atom of the thioether, occur unchanged both in the product (4) and also in the starting material. Consequently, a selective chlorination during the reaction would not be expected in which the product (4) is formed directly. For this reason, all methods known in the literature use a stepwise reaction.

Moreover, at temperatures higher than –65° C., the N-chloroaniline is able to convert to an aromatic chlorinated in the ring, and also form other oxidation products (dimers). It is therefore not surprising that the acetanilide which is significantly less electron-rich and thus significantly less chlorination-reactive to the ring only forms ring chlorinations with tert-butyl hypochlorite at 0° C. (Lengyel et. al. Synth. Comm., 1998, 28 (10), 1891-1896).

Furthermore, the sulfonium intermediates (2) or (3) can eliminate in the presence of bases and form the reactive byproduct (5), which would condense, e.g. with an aniline, as a result of which the secondary component (6) is produced irreversibly (see scheme 4). This corresponds to the so-called Pummerer oxidation of the R2-CH—R3 radical.

Scheme 4-Possible secondary reactions (for names see scheme 3):

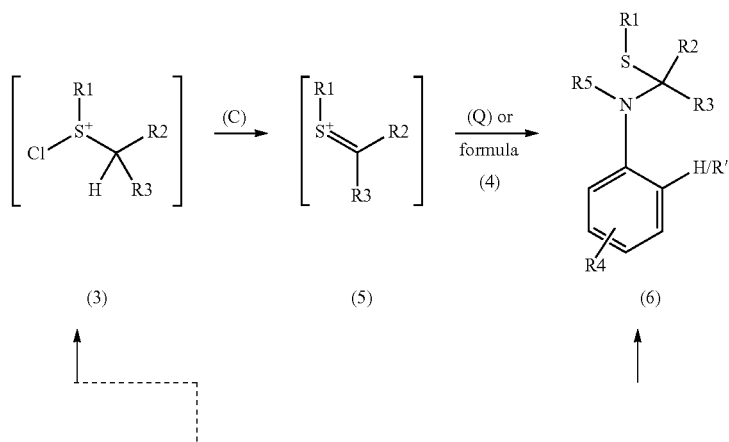

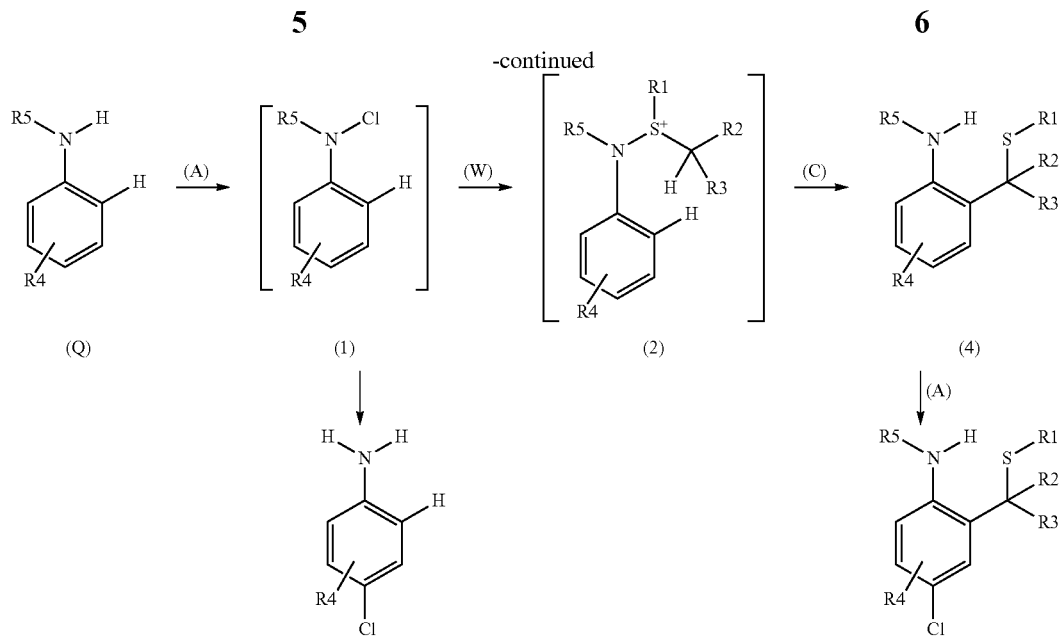

It was therefore the object to provide a modified process which permits a preparation, improved compared to the aforementioned processes, of compounds (4) via intermediates (2) (sulfonium salts) on an industrial scale with advantages such as improved overall yield and/or product purity, reduced use of starting materials, omission of further auxiliaries (such as, e.g. a second base) or simplified process course (such as, e.g. reactions at a higher temperature) or use of industrially more suitable solvents (less toxic, better recoverable).

The compounds (4) prepared in this way should preferably also permit further processing to oxindoles (1,3-dihydro-2H-indol-2-ones), which may likewise be intermediates for the synthesis of fine chemicals and active ingredients from pharmacy and/or agriculture.

SUMMARY OF THE INVENTION

Surprisingly, it has now been found that, despite the aforementioned problems, the reaction could be modified in such a way that it can be carried out on an industrially realizable scale.

The invention provides a process for the preparation of compounds of formula (4):

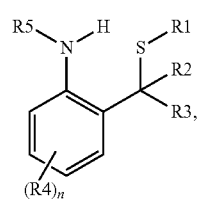

where
R1=C1-C6 alkyl, substituted alkyl, aryl or substituted aryl, preferably C1-C4 alkyl;
R2=H, C1-C6 alkyl or substituted alkyl;
R3=electron-withdrawing or activating group, such as —CO—R1; —CO—X, where X=OR1, SR1, NR2R2', where R2' is defined like R2 and may be identical to or different from R2; R2 and R2' can form a ring; SO(n')—R1, where n'=may be 0, 1 or 2; —CN; —NO$_2$, aryl or heteroaryl;
R4=F, Cl, Br, I, CF$_3$, CN, NO$_2$, COX; where X=OR1, SR1, NR2R2', where R2' is defined like R2 above and may be identical to or different from R2, preferably F or Cl, in particular 2-F;
n=1-4, preferably 1-2, in particular 1;
R5=H, C1-C6 alkyl or substituted alkyl,
which comprises reacting a mixture
of an aniline (compound of formula Q):

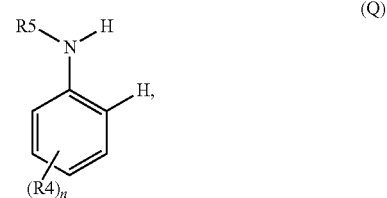

in which the radicals R4, n and R5 are as defined in formula (4),
with a thioether (compound of formula W):

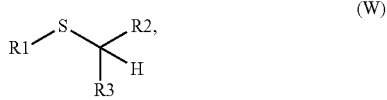

in which the radicals R1, R2 and R3 are as defined in formula (4),
in the presence of a chlorinating agent and an organic solvent at a reaction temperature in the range above −65° C., preferably between −60 and −10° C., in particular between −50 and −20° C., to give the compound of formula (4) via the mechanistically stipulated intermediate of formula (2).

DETAILED DESCRIPTION OF A PREFERRED EMBODIMENT

The selective and clean reaction with good yields resulting therefrom is particularly surprising and stands in contrast to the school of thought according to which it is described that good yields can only be achieved if the unstable N-chloro (1) or N-sulfonium (2) intermediates (see scheme 2) are formed below −65° C., in the normal case at −78° C. (Gassman et. al., J. Am. Chem. Soc., 1974, 96(17), 5508; Gassman et al., J. Am. Chem. Soc., 1974, 96(17), 5512; WO 96/41799 A1).

The thioether (compound of formula W) used in the process according to the invention has the following structure:

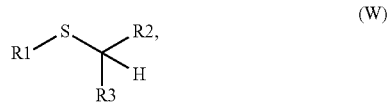

where
R1=C1-C6 alkyl, substituted alkyl, aryl or substituted aryl, preferably C1-C4 alkyl;
R2=H, C1-C6 alkyl or substituted alkyl;
R3=electron-withdrawing or activating group, such as —CO—R1; —CO—X, where X=OR1, SR1, NR2R2', where R2' is defined like R2 and may be identical to or different from R2; R2 and R2' can form a ring; SO(n')-R1, where n'=may be 0, 1 or 2; —CN; —NO$_2$, aryl or heteroaryl.

Wherever reference is made to thioether hereinbelow, the compound given above is intended.

The aniline (compound of formula Q) used in the process according to the invention has the following structure:

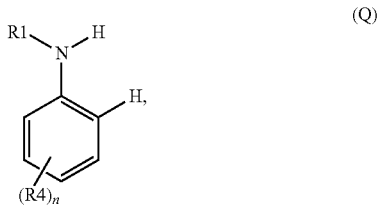

where
R4=F, Cl, Br, I, CF$_3$, CN, NO$_2$, COX;
    where X=OR1, SR1, NR2R2', where R2' is defined like R2 above and may be identical to or different from R2, preferably F or Cl, in particular 2-F;
n=1-4, preferably 1-2, in particular 1;
R5=H, C1-C6 alkyl or substituted alkyl.

It is obligatory that a hydrogen atom is present in the ortho position relative to the nitrogen atom of the aniline. The ring can be substituted with one or more substituents R4. Wherever reference is made to aniline hereinbelow, the compound given above is intended.

Suitable chlorinating agents are all chlorinating agents known to the person skilled in the art for this purpose, such as trichloroisocyanuric acid, tert-butyl hypochlorite and sulfuryl chloride. Preference is given to chlorinating agents such as sulfuryl chloride (SO$_2$Cl$_2$), which surprisingly generate, in contrast to the opinion in the literature, HCl without a second, non-nucleophilic base having to be used.

The reaction in the process according to the invention can be carried out with various solvents.

For example, it is possible to use nonpolar organic solvents, such as chloroalkanes (for example dichloromethane and dichloroethane), aromatics (for example benzene, toluene, xylene), haloaromatics (for example chlorobenzene, dichlorobenzene), substituted aromatics (for example benzotrifluoride, chlorobenzotrifluoride, chlorotoluene, chloroxylene) alone or as mixtures with one another or as mixtures with alkanes and cycloalkanes.

In addition, however, polar organic solvents are also suitable. This is contrary to the teaching of Gassman (J. Am. Chem. Soc., 1972, 94, 3891), according to which N-chloro derivatives are less stable in polar solvents. For example, the reaction in the process according to the invention can preferably be carried out in an ester solvent, such as, for example, C1-C6 alkyl acetate (for example methyl acetate, ethyl acetate, n-propyl acetate, isopropyl acetate, 2-methylprop-1-yl acetate, n-butyl acetate, but-2-yl acetate, pentyl acetates, hexyl acetates and cycloalkyl acetates, C1-C6 alkyl and cycloalkyl propionates, C1-C6 alkyl and cycloalkyl n-butyrates, isobutyrates, pentanoates and hexanoates and cyclopentanoates and cyclohexanoates) or in mixtures thereof or in a mixture with other solvents. Compared with other solvents, such as e.g. the dichloromethane used in the literature, ester solvents have the advantage that they are industrially more suitable (less toxic, better recoverable).

The process according to the invention for the preparation of compounds of formula (4) is based on the fact that the two compounds aniline (compound of formula Q) and thioether (compound of formula W) can be advantageously premixed.

The selective and clean reaction resulting therefrom is particularly surprising and stands in contrast to the school of thought according to which Gassman demonstrated that, depending on the substituent, N-chlorination or S-chlorination is optimal for the reaction (Gassman, J. Am. Chem. Soc., 1974, 96(17), 5512). Furthermore, a mixture consisting of aniline and thioether would not be expected to exhibit selectivity during a chlorination, which is why, according to the school of thought hitherto, the process has only been carried out stepwise.

For good product yields it has been found that it is advantageous to use up to 1 equivalent, preferably 0.5 to 1.0 equivalent, particularly preferably 0.7 to 1.0 equivalent, especially preferably 0.8 to 0.95 equivalent, of the chlorinating agent. The chlorinating agent is added to a mixture of one equivalent of the thioether (compound of formula W) and an industrially economic excess of the aniline (compound of formula Q) of 2.0 to 5.0 equivalents, preferably 2.0 to 3.0 equivalents, particularly preferably 2.0 to 2.5 equivalents.

The chlorinating agent can preferably be prediluted with a solvent or a solvent mixture and can preferably be prechilled.

It is a particular embodiment of the invention that, for good product yields, also a part amount of the aniline (between 1 and 99% by weight, preferably between 20 and 80% by weight, particularly preferably 30 to 70% by weight, of the total amount of aniline) is added separately from, but simultaneously or partially simultaneously with the chlorinating agent.

One particular embodiment of the invention with regard to a simplified (industrial) process course is that, in the process according to the invention for the preparation of compounds of formula (4) it is possible to dispense with the addition of an additional tertiary amine, as a result of which re-use of the unreacted, reisolated aniline (compound of formula Q) is simplified.

Thus, it has been found that an excess of the surprisingly low-electron anilines acts as a mild base during the formation of product of formula (4). This is surprising compared with the standard Gassman reaction which uses the addition of an additional tertiary amine (cf. schemes 2 and 3: C=tertiary amine base, e.g.: triethylamine). The aniline is obviously able to catalyze the rearrangement to the product of formula (4) and therefore also to eliminate HCl from a chlorosulfonium intermediate of formula (3), which would only lead to secondary reactions. Nevertheless and precisely because of this, it is very surprising that the reaction can be carried out in this way. At the same time, the omission of an additional tertiary amine in the process according to the invention is advantageous since it is possible to dispense with a subsequent complex separation of recovered aniline and tertiary amine.

The invention also provides the process for the preparation of compounds of formulae (7) and (8):

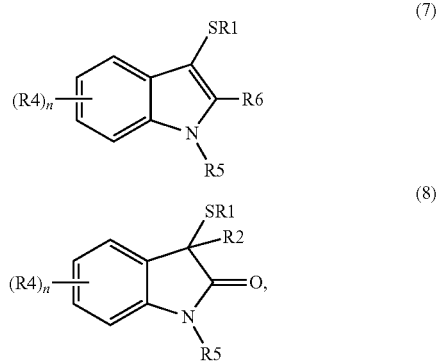

in which
R1=C1-C6 alkyl, substituted alkyl, aryl or substituted aryl, preferably C1-C4 alkyl;
R2=H, C1-C6 alkyl or substituted alkyl;
R4=F, Cl, Br, I, CF$_3$, CN, NO$_2$, COX; where X=OR1, SR1, NR2R2', where R2' is defined like R2 above and may be identical to or different from R2, preferably F or Cl, in particular 2-F;
n=1-4, preferably 1-2, in particular 1;
R5=H, C1-C6 alkyl or substituted alkyl;
R6=C1-C6 alkyl or substituted alkyl, preferably C1-C4 alkyl or OH;
where compounds of formula (4):

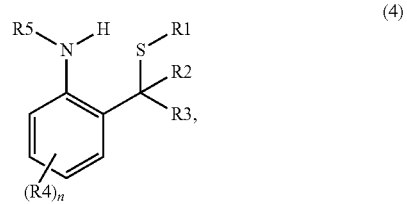

with the aforementioned definitions of the radicals R1, R2, R4 and R5 and where R3 is an electron-withdrawing or activating group, such as —CO—R1; —CO—X, where X=OR1, SR1, NR2R2', where R2' is defined like R2 and may be identical to or different from R2; R2 and R2' can form a ring; SO(n')—R1, where n' may be 0, 1 or 2; —CN; —NO$_2$, aryl or heteroaryl;
prepared by the above-described process according to the invention for the preparation of compounds of formula (4), are reacted without isolation of the compounds of formula (4), optionally in the presence of an acid catalyst, to give the indole of formula (7) or the oxindole of formula (8).

In the case of R3=CO—R1, the indole of formula (7) is obtained, whereas in the case of R3=COX, the oxindole of formula (8) or the indole of formula (7) where R6=OH is obtained. Consequently, within the context of the present invention, these specific indoles are therefore also encompassed by the term "oxindole".

For the acid catalyst in the process according to the invention, it is possible to use mineral or organic acids such as H$^+$X$^-$, where X$^-$=F$^-$, Cl$^-$, Br$^-$, I$^-$, HSO$_4^-$, BF$_4^-$, H$_2$PO$_4^-$, SO$_4^{2-}$, HPO$_4^{2-}$, PO$_4^{3-}$, R'SO$_3^-$, R''HPO$_3^-$, R'''PO$_3^{2-}$, R''''CO$_2^-$, or mixtures thereof. Preference is given to using mineral acids, in particular HCl, in gaseous form or in a solvent, preferably water or alcohol. The acid catalyst used in the process according to the invention is used in amounts customary to the person skilled in the art for this purpose.

Based on the standard process by Gassman et. al. (J. Am. Chem. Soc., 1974, 96(17), 5508), a number of oxindoles or ortho-substituted anilines have been synthesized. Thus, e.g. on the route of the synthesis of a 7-fluoroisatin, the intermediate 7-fluoro-3-methylthiooxindole was synthesized (Wierenga et al., Tetrahedron Lett. 1983, 24, 2437). One example of a 7-fluoro-3-methylthio-4-nitrooxindole prepared by the Gassman process using proton sponge and triethylamine can be found in Tetrahedron Lett. 2005, 46, 4613.

The invention therefore also provides the compounds of formula (4'), which are obtainable by the above-described process according to the invention and which are novel, as intermediates for the preparation of fine chemicals and active ingredients from pharmacy or agriculture:

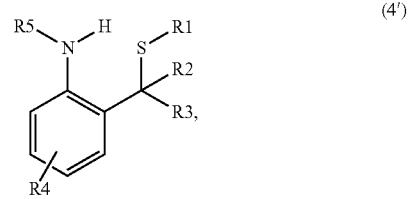

where
R1=C2-C6 alkyl, benzyl;
R2=H;
R3=CO$_2$R'', where R''= may be C1-C6 alkyl, benzyl ester;
R4=2-F, 2-Cl;
R5=H, C1-C4 alkyl.

Preference is given to compounds of formula (4'), where
R1=ethyl;
R2=H;
R3=CO$_2$-methyl, CO$_2$-ethyl;
R4=2-F, 2-Cl;
R5=H, methyl, ethyl.

The invention also provides end products of formula (7') which are obtainable by the above-described process according to the invention and which are novel:

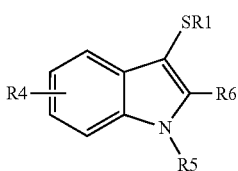

where
R1=C2-C6 alkyl, benzyl;
R4=7-F, 7-Cl;
R5=H, C1-C4 alkyl;
R6=C1-C6 alkyl.

Preference is given to compounds of formula (7'), where
R1=ethyl;
R4=7-F, 7-Cl;
R5=H, methyl;
R6=C1-C6 alkyl.

The invention also provides the compounds of formula (8'), which are obtainable by the above-described process according to the invention and which are novel, as intermediates for the preparation of fine chemicals and active ingredients from pharmacy or agriculture:

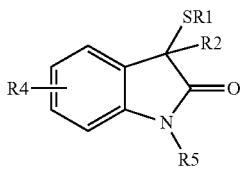

where
R1=C2-C6 alkyl, benzyl;
R2=H;
R4=7-F, 7-Cl;
R5=H, C1-C4 alkyl.

Preference is given to compounds of formula (8') where
R1=ethyl;
R2=H;
R4=7-F, 7-Cl;
R5=H, methyl.

The invention also provides for the use of the novel compounds of formulae (4'), (7') and (8') obtained according to the invention and prepared by the above-described process according to the invention for the preparation of further processing products, where the group SR1 is replaced by hydrogen via a desulfonation process known to the person skilled in the art.

In connection with the chemical terms used in this description, the definitions customary for the person skilled in the art apply unless specifically defined otherwise. The radicals alkyl, alkoxy, haloalkyl, haloalkoxy, alkylamino and alkylthio, and also the corresponding unsaturated and/or substituted radicals in the carbon backbone may in each case be straight-chain or branched. Unless specifically stated, in these radicals, the lower carbon backbones, e.g. having 1 to 6 carbon atoms, or in the case of unsaturated groups having 2 to 6 carbon atoms, are preferred. Alkyl radicals, including in the composite meaning such as alkoxy, haloalkyl etc., are e.g. methyl, ethyl, n-propyl or isopropyl, n-, iso-, t- or 2-butyl, pentyls, hexyls, such as n-hexyl, isohexyl and 1,3-dimethylbutyl, heptyls, such as n-heptyl, 1-methylhexyl and 1,4-dimethylpentyl.

Cycloalkyl is a carbocyclic, saturated ring system having preferably 3 to 8 carbon atoms, e.g. cyclopropyl, cyclobutyl, cyclopentyl or cyclohexyl.

Halogen is, for example, fluorine, chlorine, bromine or iodine. Haloalkyl is alkyl partially or completely substituted by halogen, preferably by fluorine, chlorine and/or bromine, in particular by fluorine and/or chlorine, e.g. monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is e.g. $OCF_3$, $OCHF_2$, $OCH_2F$, $CF_3CF_2O$, $OCH_2CF_3$ and $OCH_2CH_2Cl$; the same applies for other radicals substituted by halogen.

Aryl is a mono-, bi- or polycyclic aromatic system, for example phenyl, naphthyl, tetrahydronaphthyl, indenyl, indanyl, pentalenyl, fluorenyl and the like, preferably phenyl.

A heterocyclic radical or ring (heterocyclyl) may be saturated, unsaturated or heteroaromatic; it contains preferably one or more, in particular 1, 2 or 3 heteroatoms in the heterocyclic ring, preferably from the group N, O and S; it is preferably an aliphatic heterocyclyl radical having 3 to 7 ring atoms or a heteroaromatic radical having 5 or 6 ring atoms. The heterocyclic radical may be e.g. a heteroaromatic radical or ring (heteroaryl), such as e.g. a mono-, bi- or polycyclic aromatic system in which at least 1 ring contains one or more heteroatoms, for example pyridyl, pyrimidinyl, pyridazinyl, pyrazinyl, triazinyl, thienyl, thiazolyl, thiadiazolyl, oxazolyl, isoxazolyl, furyl, pyrrolyl, pyrazolyl and imidazolyl, or is a partially or completely hydrogenated radical such as oxiranyl, pyrrolidyl, piperidyl, piperazinyl, dioxolanyl, oxazolinyl, isoxazolinyl, oxazolidinyl, isoxazolidinyl, morpholinyl, tetrahydrofuryl. Suitable substituents for a substituted heterocyclic radical are the substituents given below, additionally also oxo. The oxo group can also occur on the heteroring atoms, which can exist in various oxidation states, e.g. in the case of N and S.

Substituted radicals, such as a substituted alkyl, aryl, phenyl, benzyl, heterocyclyl and heteroaryl radical, are, for example, a substituted radical derived from the unsubstituted basic body, where the substituents are, for example, one or more, preferably 1, 2 or 3, radicals from the group halogen, alkoxy, haloalkoxy, alkylthio, hydroxy, amino, nitro, carboxy, cyano, azido, alkoxycarbonyl, alkylcarbonyl, formyl, carbamoyl, mono- and dialkylaminocarbonyl, sulfamoyl, mono- and dialkylaminosulfonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl and haloalkyl; in the term "substituted radicals", such as substituted alkyl etc., in addition to the specified saturated hydrocarbon-containing radicals, corresponding unsaturated aliphatic and aromatic radicals, such as optionally substituted phenyl, phenoxy etc., are included as substituents. For radicals with carbon atoms, preference is given to those having 1 to 4 carbon atoms, in particular 1 or 2 carbon atoms. Preference is generally given to substituents from the group consisting of halogen, e.g. fluorine and chlorine, (C1-C4)alkyl, preferably methyl or ethyl, (C1-C4)haloalkyl, preferably trifluoromethyl, (C1-C4) alkoxy, preferably methoxy or ethoxy, (C1-C4)haloalkoxy, nitro and cyano. Particular preference is given here to the substituents methyl and fluorine.

The formulae (4'), (7') and (8') also include, if applicable, all stereoisomers. Such compounds contain one or more asymmetric carbon atoms which are not stated separately in the general formulae. The possible stereoisomers defined by their specific spatial form, such as enantiomers, diastereomers, can be obtained by customary methods from mixtures of the stereoisomers or else can be prepared by stereoselective reactions in combination with the use of stereochemically pure starting substances.

The compounds of formulae Q and W to be used according to the invention are known or can be prepared analogously to generally known processes.

The process according to the invention for obtaining compounds of formula (4) is carried out, for example, by initially introducing aniline (compound of formula Q) and thioether (compound of formula W) in the solvent and, preferably under protective gas, cooling. A mixture of chlorinating agent and solvent is added dropwise to this stirred solution. The reaction is then heated and diluted with an aqueous acid. The phases are separated and the organic phase is washed with an aqueous acid. The organic phase is then dried and if the compound of formula (4) is a solid, concentrated in vacuo, and possibly an antisolvent is added and the mixture is stirred for several hours. The solid (compound of formula (4)) is filtered off and washed with the antisolvent or solvent mixture. If the compound of formula (4) is an oil, the organic phase is concentrated in vacuo.

The process according to the invention for obtaining compounds of formulae (7) and (8) is carried out, for example, by initially introducing aniline (compound of formula Q) and thioether (compound of formula W) in the solvent and, preferably under protective gas, cooling. A mixture of chlorinating agent and solvent is added dropwise to this stirred solution. The reaction is then heated and diluted with an aqueous acid. The phases are separated and the organic phase is washed with an aqueous acid. The organic phase is then, possibly for compounds of formula (7) and preferably for compounds of formula (8), admixed with an acid catalyst and stirred for several hours. 90% of the solvent is then removed in vacuo and an antisolvent is added and the mixture is stirred for several hours. The solid (compound of formula (7) or (8)) is filtered off and washed with the antisolvent or solvent mixture.

The examples below illustrate the process according to the invention in more detail without limiting the process according to the invention thereto. In the examples below, quantitative data refer to the weight, unless specifically defined otherwise (in the description, % by wt.=percent by weight was used analogously for this). For measurement units, physical parameters and the like, customary abbreviations are used, for example h=hour(s), m.p.=melting point, l=liter, ml=milliliter, g=gram, min=minute(s), in vacuo=under reduced pressure, of theory=percent yield according to theory.

SYNTHESIS EXAMPLE 1

2-Chloroaniline (20.4 g) and methyl methylmercaptoacetate (8.36 g) were initially introduced into chlorobenzene (77 ml) and cooled to −30° C. under protective gas. A solution of sulfuryl chloride (8.45 g) in chlorobenzene (67 ml) was added dropwise to this stirred solution in 30 minutes. The reaction mixture was warmed to −5° C. and diluted with 0.4N hydrochloric acid (110 ml). The phases were separated and the organic phase was washed with 0.4N hydrochloric acid (4×110 ml). The organic phase was then admixed with 10% strength HCl in MeOH (2 ml) and stirred for 16 hours. 90% of the solvent was removed in vacuo, heptane (120 ml) was added and the mixture was stirred for 4 hours. The solid was filtered off and washed with heptane (2×50 ml). This gives 7-chloro-3-methylthiooxindole (9.36 g, 70% of theory). m.p.: 167-170° C.

SYNTHESIS EXAMPLE 2

2-Chloroaniline (20.4 g) and methyl methylmercaptoacetate (8.36 g) were initially introduced into chlorobenzene (77 ml) and cooled to −30° C. under protective gas. A solution of sulfuryl chloride (8.45 g) in chlorobenzene (67 ml) was added dropwise to this stirred solution in 30 minutes. The reaction mixture was warmed to −5° C. and diluted with 0.4N hydrochloric acid (110 ml). The phases were separated and the organic phase was washed with 0.4N hydrochloric acid (4×110 ml) and water (50 ml) and dried over sodium sulfate. The organic phase was filtered and distilled in vacuo. This gives methyl (2-amino-3-chlorophenyl)(methylthio)acetate as brown-red oil (10.9 g, 71% of theory).

SYNTHESIS EXAMPLE 3

4-Chloroaniline (20.4 g) and methyl methylmercaptoacetate (8.36 g) were initially introduced into n-butyl acetate (77 ml) and cooled to −30° C. under protective gas. A solution of sulfuryl chloride (8.45 g) in n-butyl acetate (67 ml) was added dropwise to this stirred solution in 30 minutes. The reaction mixture was warmed to 10° C. and diluted with 0.4N hydrochloric acid (110 ml). The phases were separated and the organic phase was washed with 0.4N hydrochloric acid (2×110 ml). The organic phase was then admixed with 10% strength HCl in MeOH (2 ml) and stirred for 16 hours. 90% of the solvent was removed in vacuo, heptane (120 ml) was added and the mixture was stirred for 4 hours. The solid was filtered off and washed with heptane (2×50 ml). This gives 5-chloro-3-methylthiooxindole (7.89 g, 59% of theory). m.p.: 154-157° C.

SYNTHESIS EXAMPLE 4

2-Fluoroaniline (17.8 g) and methyl methylmercaptoacetate (8.36 g) were initially introduced into n-butyl acetate (77 ml) and cooled to −30° C. under protective gas. A solution of sulfuryl chloride (8.45 g) in n-butyl acetate (67 ml) was added dropwise to this stirred solution in 30 minutes. The reaction mixture was warmed to 10° C. and diluted with 0.4N hydrochloric acid (110 ml). The phases were separated and the organic phase was washed with 0.4N hydrochloric acid (1×110 ml). The organic phase was then admixed with 10% strength HCl in MeOH (2 ml) and stirred for 16 hours. 90% of the solvent was removed in vacuo, heptane (120 ml) was added and the mixture was stirred for 4 hours. The solid was filtered off and washed with heptane (2×50 ml). This gives 7-fluoro-3-methylthio-oxindole (9.17 g, 72% of theory). m.p.: 156-159° C.

SYNTHESIS EXAMPLE 5

2-Fluoroaniline (17.8 g) and methyl methylmercaptoacetate (8.36 g) were initially introduced into n-butyl acetate (77 ml) and cooled to −30° C. under protective gas. A solution of sulfuryl chloride (8.45 g) in n-butyl acetate (67 ml) was added dropwise to this stirred solution in 30 minutes. The reaction mixture was warmed to 10° C. and diluted with 0.4N hydrochloric acid (110 ml). The phases were separated and the organic phase was washed with 0.4N hydrochloric acid (1×110 ml) and water (50 ml) and dried over sodium sulfate. The organic phase was filtered and distilled in vacuo. This gives methyl (2-amino-3-fluorophenyl)(methylthio)acetate as brown oil (12.5 g, 73% of theory).

SYNTHESIS EXAMPLE 6

2-Fluoroaniline (17.8 g) and methyl methylmercaptoacetate (8.36 g) were initially introduced into n-butyl acetate (77 ml) and cooled to −50° C. under protective gas. A solution of sulfuryl chloride (8.45 g) in n-butyl acetate (67 ml) was added dropwise to this stirred solution in 30 minutes at an internal temperature of from −53 to −48° C. The reaction mixture was warmed to 10° C., diluted with 0.4N hydrochloric acid (110 ml) and then stirred for 5 min. The phases were separated and the organic phase was washed with 0.4N hydrochloric acid (1×110 ml). The organic phase was admixed with conc. HCl (0.2 ml). The reaction mixture was stirred for 24 hours, admixed once again with conc. HCl (0.05 ml) and left to stand for 16 hours at 4° C. Approximately 90% of the solvent was removed in vacuo, heptane (120 ml) was added and the mixture was stirred for 5 hours. The solid was filtered off, washed with heptane (2×50 ml) and dried. This gives 7-fluoro-3-methylthio-oxindole (8.71 g, 63% of theory). LCMS: M+H=198 (100%). The $^1$H-NMR R is in agreement with that described in synthesis example 7.

SYNTHESIS EXAMPLE 7

2-Fluoroaniline (18.1 g) and methyl methylmercaptoacetate (8.58 g) were initially introduced into n-butyl acetate (80 ml) and cooled to −20° C. under protective gas. A solution of sulfuryl chloride (8.77 g) in n-butyl acetate (70 ml) was added dropwise to this stirred solution in 30 minutes at an internal temperature of from −25 to −18° C. The reaction mixture was warmed to 10° C. over the course of 60 min and diluted with 0.4N hydrochloric acid (110 ml). The phases were separated and the organic phase was washed with 0.4N hydrochloric acid (1×110 ml). The organic phase was then admixed with conc. hydrochloric acid (0.5 ml) and MeOH (2 ml) and stirred for 16 hours. Approximately 90% of the solvent was removed in vacuo, n-heptane (120 ml) was added and the mixture was stirred for 3 hours. The solid was filtered off and washed with heptane. This gives 7-fluoro-3-methylthio-oxindole (7.85 g, 55% of theory). 1H-NMR (CDCl$_3$): d=2.06 (s, 3H), 4.32 (s, 1H), 7.02-7.05 (m, 2H), 7.17-7.19 (m, 1H), 8.3 (s, broad, 1H).

SYNTHESIS EXAMPLE 8

2-Fluoroaniline (17.8 g) and methyl methylmercaptoacetate (8.36 g) were initially introduced into dichloromethane (77 ml) and cooled to −30° C. under protective gas. A solution of sulfuryl chloride (8.45 g) in n-butyl acetate (67 ml) was added to this stirred solution in 30 minutes at an internal temperature of from −33 to −28° C. The reaction mixture was warmed to 10° C., diluted with 0.4N hydrochloric acid (110 ml) and then stirred for 5 min. The phases were separated and the organic phase was washed with 0.4N hydrochloric acid (1×110 ml). The organic phase was then admixed with conc. HCl (0.2 ml). The reaction mixture was stirred for 16 hours, admixed with conc. HCl (0.05 ml), stirred for 7 hours, admixed once again with conc. HCl (0.05 ml) and then stirred for 16 hours. Approximately 90% of the solvent was removed in vacuo, heptane (110 ml) was added and the mixture was stirred for 5 hours. The solid was filtered off, washed with heptane (2×50 ml) and dried. This gives 7-fluoro-3-methylthio-oxindole (5.84 g, 42% of theory). LCMS and 1H-NMR are in agreement with those described in synthesis examples 6 and 7.

SYNTHESIS EXAMPLE 9

2-Fluoroaniline (7.73 g) and methyl methylmercaptoacetate (8.36 g) were initially introduced into n-butyl acetate (67 ml) and cooled to −35° C. under protective gas. A solution of sulfuryl chloride (8.45 g) in n-butyl acetate (67 ml) was metered into this stirred solution and, in parallel to this, 2-fluoroaniline (10.04 g) in n-butyl acetate (10 ml) was metered directly into the reaction solution in 25 minutes, during which the temperature increased to −29° C. After 15 minutes at −30° C., the reaction mixture was warmed to 10° C. and 0.4N hydrochloric acid (110 ml) was added dropwise. The phases were separated and the organic phase was washed with 0.4N hydrochloric acid (1×110 ml). The organic phase was admixed with 10% strength HCl in MeOH (1.9 ml) and stirred for 16 hours. 95% of the solvent was removed in vacuo, heptane (120 ml) was added and the reaction mixture was stirred for 3 hours. The solid was filtered off and washed with heptane (2×50 ml). This gives 7-fluoro-3-methylthio-oxindole (8.87 g, 70.0% of theory).

SYNTHESIS EXAMPLE 10

2-Fluoroaniline (18.1 g) and 1-(methylsulfanyl)acetone (7.44 g) were initially introduced into n-butyl acetate (80 ml) and cooled to −30° C. under protective gas. With stirring, a solution of sulfuryl chloride (8.77 g) in n-butyl acetate (70 ml) was added dropwise over the course of 30 minutes and the mixture was then stirred for 1.5 hours at an internal temperature of from −35 to −28° C. The reaction mixture was warmed to 0° C. and the phases were separated. The organic phase was extracted with 0.5N hydrochloric acid (2×80 ml) and water (40 ml), dried with a small amount of sodium sulfate and concentrated by evaporation in vacuo. The residue is admixed three times with ethyl acetate and concentrated by evaporation. This gives 7-fluoro-3-methylthio-oxindole as brown oil (9.67 g, 59% of theory). 1H-NMR (CDCl$_3$): d=2.26 (s, 3H), 2.55 (s, 3H), 6.87 (dd, 1H), 7.03-7.08 (m, 1H), 7.43 (d, 1H), 8.24 (s, broad, 1H). LCMS: M+H=196.

The invention claimed is:
1. A process for the preparation of compounds of formulae (7) and (8):

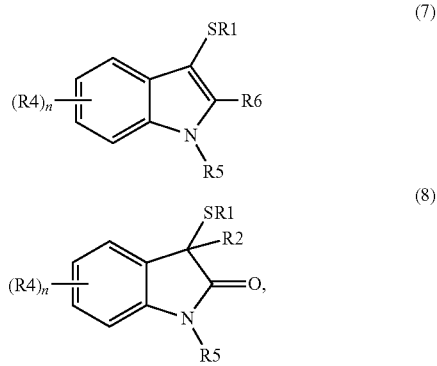

in which
R1=C1-C6 alkyl, substituted alkyl, aryl or substituted aryl,
R2=H, C1-C6 alkyl or substituted alkyl;
R4=F, Cl, Br, I, CF$_3$, CN, NO$_2$, COX;
where X=OR1, SR1, NR2R2', where R2' is defined like R2 above and may be identical to or different from R2,
n=1-4,
R5=H, C1-C6 alkyl or substituted alkyl;
R6=C1-C6 alkyl or substituted alkyl or OH;

where compounds of formula (4):

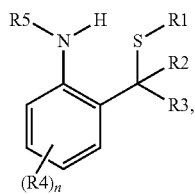

with the aforementioned definitions of the radicals R1, R2, R4, n and R5 and where R3 is an electron-withdrawing or activating group are prepared by a process comprises reacting a mixture
of an aniline (compound of formula Q):

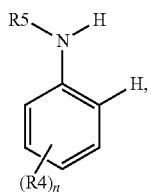

in which the radicals R4, n and R5 are as defined in formula (4),
with a thioether (compound of formula W):

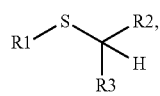

in which the radicals R1, R2 and R3 are as defined in formula (4),
in the presence of a chlorinating agent and an organic solvent at a reaction temperature in the range between −60 and −10° C.; wherein the addition of an additional tertiary amine is dispensed with to give the compound of formula (4)
and wherein the prepared compounds of formula (4) are reacted without isolation of the compounds of formula (4), optionally in the presence of an acid catalyst, to give the indole of formula (7) or the oxindole of formula (8).

2. The process as claimed is claim 1, wherein
where
R1=C2-C6 alkyl or benzyl;
R2=H;
R4=2-F or 2-Cl;
R5=H or C1-C4 alkyl.

3. The process as claimed in claim 1, wherein
R1=C2-C6 alkyl or benzyl;
R4=7-F or 7-Cl;
R5=H or C1-C4 alkyl;
R6=C1-C6 alkyl.

4. The process as claimed in claim 1, wherein
R1=C2-C6 alkyl or benzyl;
R2=H;
R4=7-F or 7-Cl;
R5=H or C1-C4 alkyl;
as intermediate for the preparation of a fine chemical and/or active ingredient from pharmacy or agriculture.

5. The process as claimed in claim 1, wherein a compound of formula (7) is produced.

6. The process as claimed in claim 1, wherein a compound of formula (8) is produced.

7. The process as claimed in claim 1, wherein said acid catalyst is used.

8. The process as claimed in claim 1, wherein the reaction temperature is between −50 and −20° C.

9. The process as claimed in claim 1, wherein R1 is C1-C4 alkyl, R4 is F or Cl, and n is 1.

10. The process as claimed in claim 1, wherein the chlorinating agent comprises sulfuryl chloride.

11. The process as claimed in claim 1, wherein the organic solvent comprises an ester solvent.

12. The process as claimed in claim 7, wherein the acid comprises hydrochloric acid.

* * * * *